(12) United States Patent
Tanji et al.

(10) Patent No.: US 6,461,342 B2
(45) Date of Patent: Oct. 8, 2002

(54) DISPOSABLE SANITARY GARMENT

(75) Inventors: Hiroyuki Tanji; Takamitsu Igaue, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 27 days.

(21) Appl. No.: 09/727,041

(22) Filed: Nov. 30, 2000

(65) Prior Publication Data
US 2001/0039408 A1 Nov. 8, 2001

(30) Foreign Application Priority Data
Nov. 30, 1999 (JP) ............................................ 11-339285

(51) Int. Cl.⁷ ................................................ A61F 13/15
(52) U.S. Cl. ........................ 604/385.25; 604/385.26; 604/385.27; 604/385.28; 604/385.21
(58) Field of Search ..................... 604/385.25, 385.26, 604/385.27, 385.28, 385.04, 317–407

(56) References Cited

U.S. PATENT DOCUMENTS

| | | | | |
|---|---|---|---|---|
| 4,246,900 A | * | 1/1981 | Schroder .................... 128/287 |
| 4,695,278 A | | 9/1987 | Lawson | |
| 4,834,740 A | * | 5/1989 | Suzuki et al. ............. 604/385.2 |
| 4,883,482 A | * | 11/1989 | Gandrez et al. .......... 604/385.2 |
| 5,591,151 A | * | 1/1997 | Hasse et al. .............. 604/385.1 |
| 5,607,416 A | * | 3/1997 | Yamamoto et al. .......... 604/397 |
| 5,662,636 A | * | 9/1997 | Benjamin et al. ......... 604/385.2 |
| 6,183,459 B1 | * | 2/2001 | Ymamamoto et al. .. 604/385.27 |

* cited by examiner

Primary Examiner—Jeanette Chapman
(74) Attorney, Agent, or Firm—Baker & Daniels

(57) ABSTRACT

A disposable sanitary garment includes a chassis defining an outer surface thereof, the chassis is provided along its transversely opposite side edge portions destined to extend around a wearer's thighs with a pair of first leg-hole elastic members extending circumferentially around the thighs and with a pair of second leg-hole elastic members describing a circular arc being convex inwardly of the garment. The chassis is folded back inwardly of the garment along one side edges of the respective members with the second leg-hole elastic members inside and a portion of the chassis extending inside the zone along which the chassis has been first folded back is folded back along the other side edges of the respective members.

5 Claims, 6 Drawing Sheets

DISPOSABLE SANITARY GARMENT

BACKGROUND OF THE INVENTION

This invention relates to a disposable sanitary garment such as a disposable diaper, disposable training pants or a disposable diaper cover.

U.S. Pat. No. 4,695,278 discloses a disposable diaper having at least one elastically contractible gasketing cuff and at least one barrier cuff. The gasketing cuff is formed by portions of a liquid-absorbent core sandwiching top- and backsheets laterally extending beyond a side edge of the core and placed upon each other. The gasketing cuff is provided with an elastic member extending longitudinally of the diaper and secured under tension to the gasketing cuff. The barrier cuff is formed by a belt-like sheet bonded along one of its transversely opposite side edge portions to the top surface of the topsheet. The barrier cuff is provided along its other side edge portion with an elastic member extending longitudinally of the diaper and secured under tension thereto. The elastic member of the gasketing cuff contracts and the gasketing cuff comes in leak-barrier contact with a wearer's thigh as the diaper is put on a wearer's body. At the same time, the elastic member of the barrier cuff tracts to raise the barrier cuff on the top surface of the topsheet and to form a channel opening inwardly of the diaper. Liquid excretion such as urine or loose passage is reliably obstructed by the barrier cuff raised in this manner and it is not apprehended that such excretion might leak from the diaper.

To form the barrier normally biased to rise on the top surface of the topsheet, it is necessary for the diaper of well known art to use the belt-like sheet sufficiently long to extend across a crotch region of the diaper into front and rear waist regions of the diaper. As a result, the top surface of the topsheet may become irregular and/or stiff and affect a feeling to wear the diaper. In addition, the requirement that the belt-like sheet extending longitudinally of the diaper across the crotch region into the front and rear waist regions should be used in order to form the barrier having a desired leak-barrier function conflicts with the intention to reduce the cost for manufacturing the diaper by minimizing stock material use to make the diaper.

SUMMARY OF THE INVENTION

It is an object of this invention to provide a disposable sanitary garment having a pair of barriers adapted to rise on a crotch region of the garment as the latter is put on a wearer's body and to fulfill a leak-barrier function without deterioration of a feeling to wear the garment and rise of material cost.

According to this invention, there is provided a disposable sanitary garment having inner and outer surfaces, comprising: a chassis which defines the outer surface of the sanitary garment being provided along transversely opposite side edge portions which circumferentially extend around the wearer's thighs with a pair of first leg-hole elastic members which extend along edges of the side edge portions circumferentially around the wearer's thighs and with a pair of second leg-hole elastic members which extend from the edges of the side edge portions while describing circular arcs being convex inwardly of the crotch region; the chassis being folded back inwardly of the garment along each of the second leg-hole elastic members so as to wrap the second leg-hole elastic members and a portion of the chassis which extends inside the folded zone being folded back again outwardly of the garment.

The disposable sanitary garment according to this invention is applicable also to diapers for baby, diapers for adult, training pants, diaper covers for baby or adult or the like. The term "disposable" used herein means not only that the garment should be thrown away after used once but also that the garment can be reused limited times.

The disposable sanitary garment according to this invention is provided with the substantially rectilinear first leg-hole elastic members and the circular arc describing second leg-hole elastic members to form the pair of barriers normally biased to rise up in the crotch region. Such a unique arrangement is effective to avoid the problem of the conventional barriers that the longitudinal front and rear ends of the garment might create a feeling of discomfort against the wearer and/or the material cost might be unacceptably increased.

DETAILED DESCRIPTION OF THE PREFERRED EMBODIMENTS

Details of a disposable sanitary garment according to this invention will be more fully understood from the description of a disposable diaper cover as one embodiment of this invention given hereunder with reference to the accompanying drawings.

Figure 1:
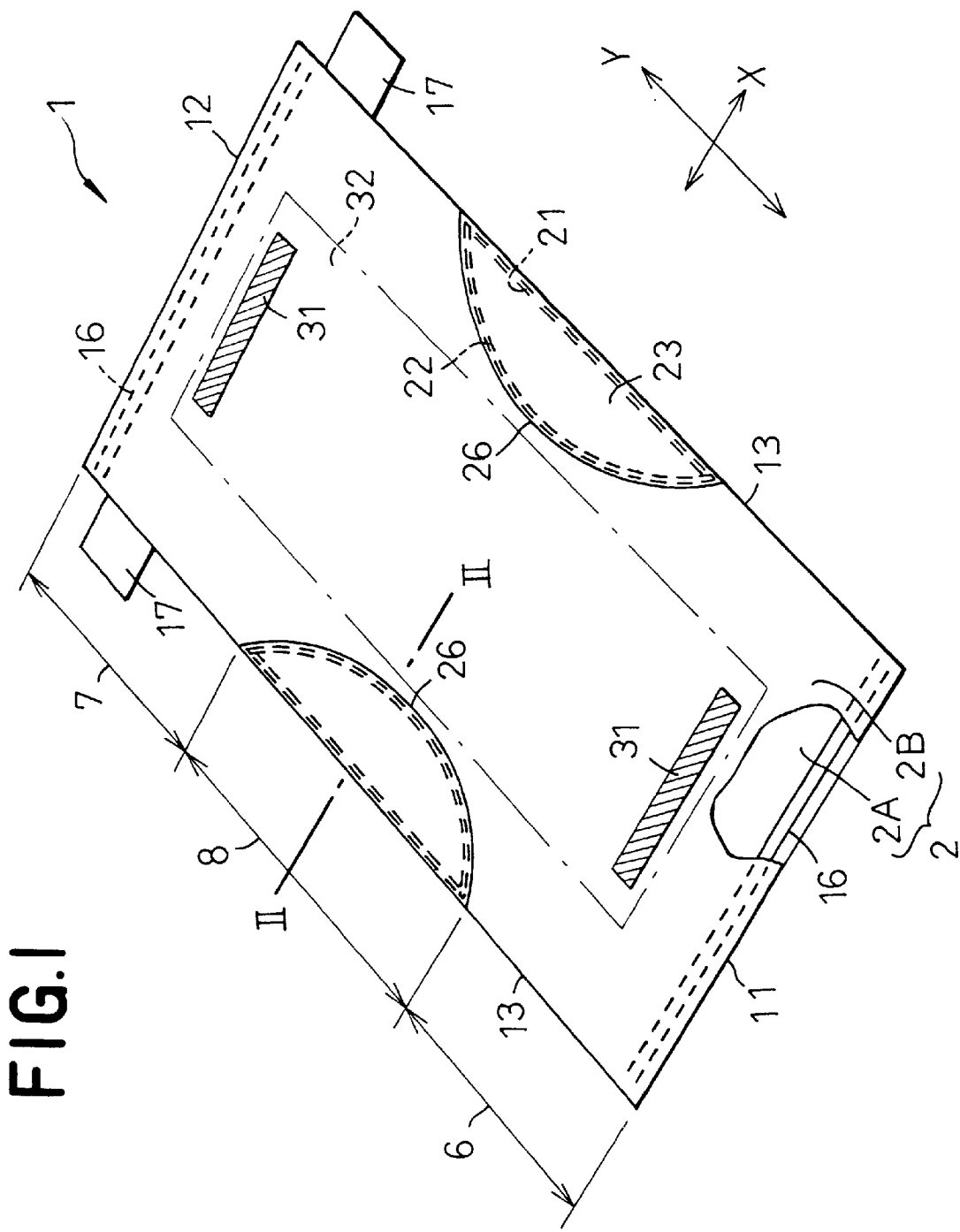
FIG. 1 is a perspective view showing a partially cutaway diaper cover according to this invention.

A diaper cover 1 shown by FIG. 1 in a perspective view is a chassis 2 composed of an outer plastic film 2A and an inner nonwoven fabric 2B laminated onto the outer plastic film 2A. The diaper cover 1 has a longitudinal direction Y and a transverse direction X and is configured to define a front waist region 6, a rear waist region 7 and a crotch region 8 extending between these two waist regions 6, 7 as viewed in the longitudinal direction Y so that these regions 6, 7, 8 may cover belly, hip and crotch of a wearer. The illustrated diaper cover 1 is substantially of a rectangular shape contoured by a longitudinally front end 11, a longitudinally rear end 12 and transversely opposite side edges 13 extending parallel to each other between the two ends 11, 12 along and inside which waist-hole elastic members 16 extend transversely of the diaper cover 1. The elastic members 16 are disposed between the plastic film 2A and the nonwoven fabric 2B and secured under tension to the inner surface of at least one of them 2A, 2B. The rear waist region 7 is provided with a pair of tape fasteners 17 laterally extending from the transversely opposite side edges 13 by means of which the front and rear waist regions 6, 7 can be connected to each other when the diaper cover 1 is put on the wearer's body. The crotch region 8 is provided along and immediately inside each of its side edges 13 with a first leg-hole elastic member 21 rectilinearly extending in the direct Y and a second leg-hole elastic member 22 extending from the side edge 13 inwardly of the diaper cover 1 and then back toward the side edge 13 to describe a circular arc which is convex inwardly of the diaper cover 1. Both these first and second leg-hole elastic members 21, 22 are disposed between the plastic film 2A and the nonwoven fabric 2B and secured under tension to the inner surface of at least one of these plastic film 2A and nonwoven fabric 2B. The first leg-hole elastic member 21 has its longitudinally opposite ends substantially placed upon those of the second leg-hole elastic member 22, i.e., those of said first leg-hole elastic member 21 are placed upon or lie closely adjacent those of the second leg-hole elastic member 22 to define a substantially semicircular side edge zone 23 destined to extend around the wearer's thigh. A circular arc describing line 26 of the side edge zone 23 corresponds to a fold line (See FIG. 2) of the chassis 2.

Such diaper cover 1 has fastening means 31 in the form of a male member or a female member of a mechanical fastener commonly known under the name of VELCRO or MAGIC TAPE or a pressure-sensitive adhesive attached to or applied on the inner surface of the diaper cover 1, respectively. Excretion disposal material 32 such as a urine-absorbent pad may be attached to the diaper cover 1 by means of such fastening means 31 before the diaper cover 1 is actually put on the wearer's body. Of the diaper cover 1 used in such manner, the plastic film 2A is of a liquid-impervious nature.

Figure 2:
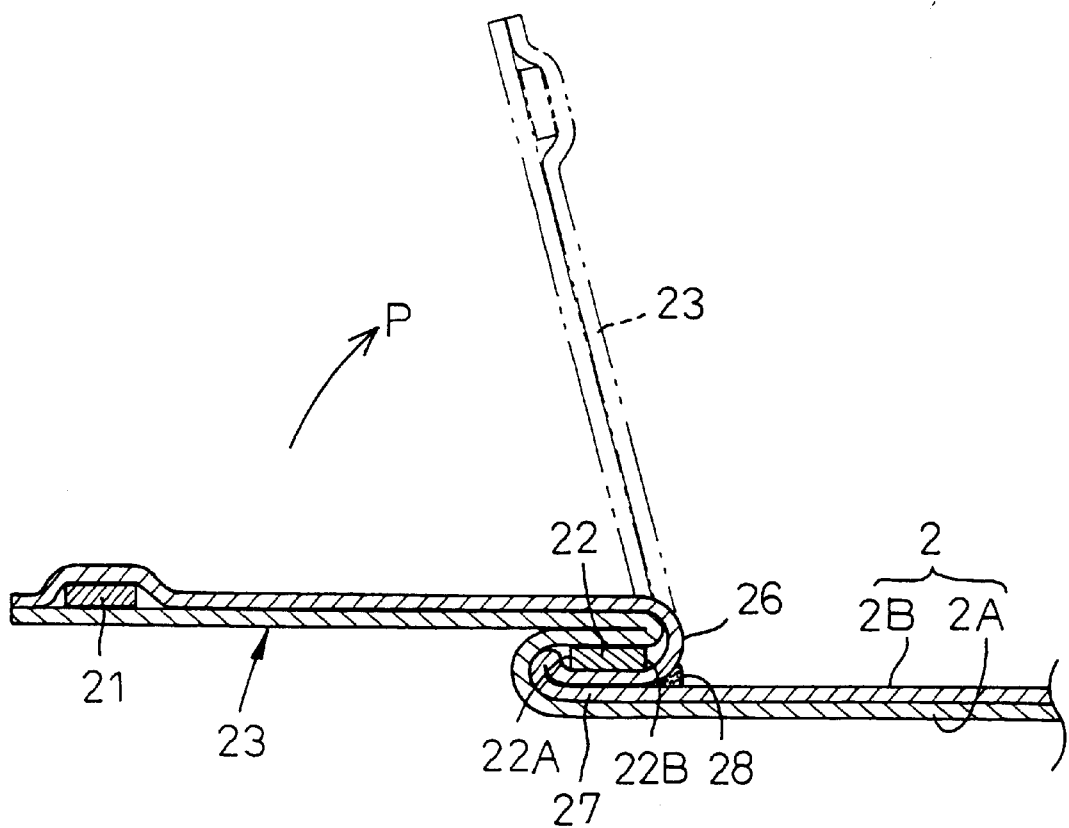
FIG. 2 is a sectional view taken along line II—II in FIG. 1.

FIG. 2 is a sectional view taken along line II—II in FIG. 1. The side edge zone 23 is formed by folding back the chassis 2 along a side edge 22A of the second leg-hole elastic member 22 inwardly of the cover 1 and then folding back a portion of the chassis 2 now lying inside the elastic member 22 along a fold line 26 extending along the other side edge 22B of the elastic member 22 outwardly of the cover 1. In the vicinity of the fold line 27, the second leg-hole elastic member 22 and opposed surfaces of the nonwoven fabric 2B are bonded one to another by an adhesive 28.

Figure 3:
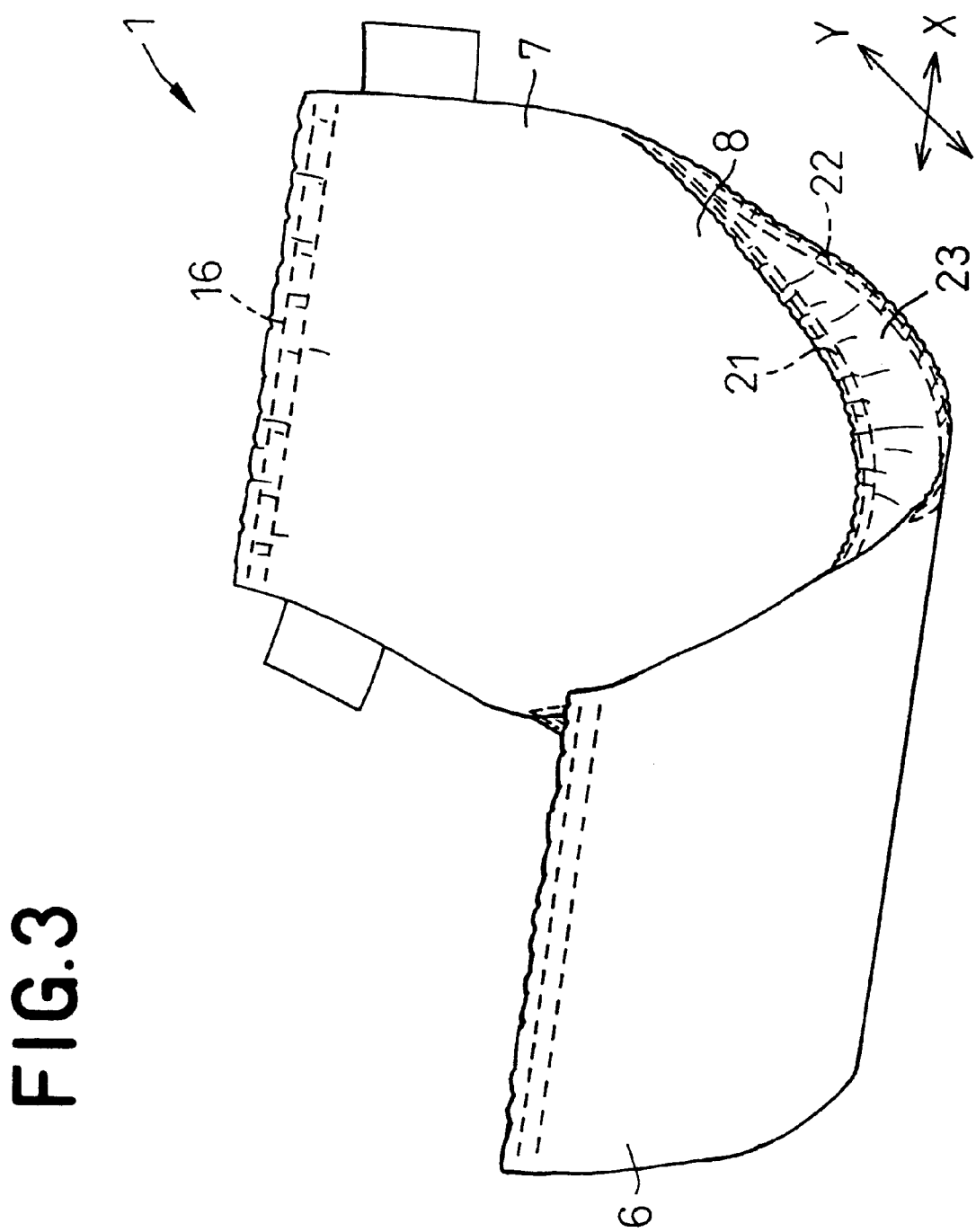
FIG. 3 is a perspective view showing the diaper cover as being curved.

FIG. 3 is a perspective view showing the diaper cover 1 as longitudinally curved. With the cover 1 being longitudinally curved, contraction of the first leg-hole elastic member 21 causes the semicircular side edge portion 23 to rise up in the crotch region 8. Specifically, the side edge portion 23 swings around its proximal end defined by the fold line 26, in a direction indicated by an arrow P in FIG. 2 and functions as a barrier to obstruct body fluids tending to flow in the transverse direction X in the crotch region 8. In the case of the illustrated diaper cover 1, contraction of the waist-hole elastic members 16 generate gathers along and inside the longitudinal front and rear ends 11, 12, respectively, and contraction of the first and second leg-hole elastic members 21, 22 generate gathers along these elastic members 21, 22, respectively. Contraction of the first and second leg-hole elastic members 21, 22 enable the semicircular side edge portion 23 to come in leak-barrier contact with the wearer's thigh at least in the vicinity of the first leg-hole elastic member 21.

Figure 4:
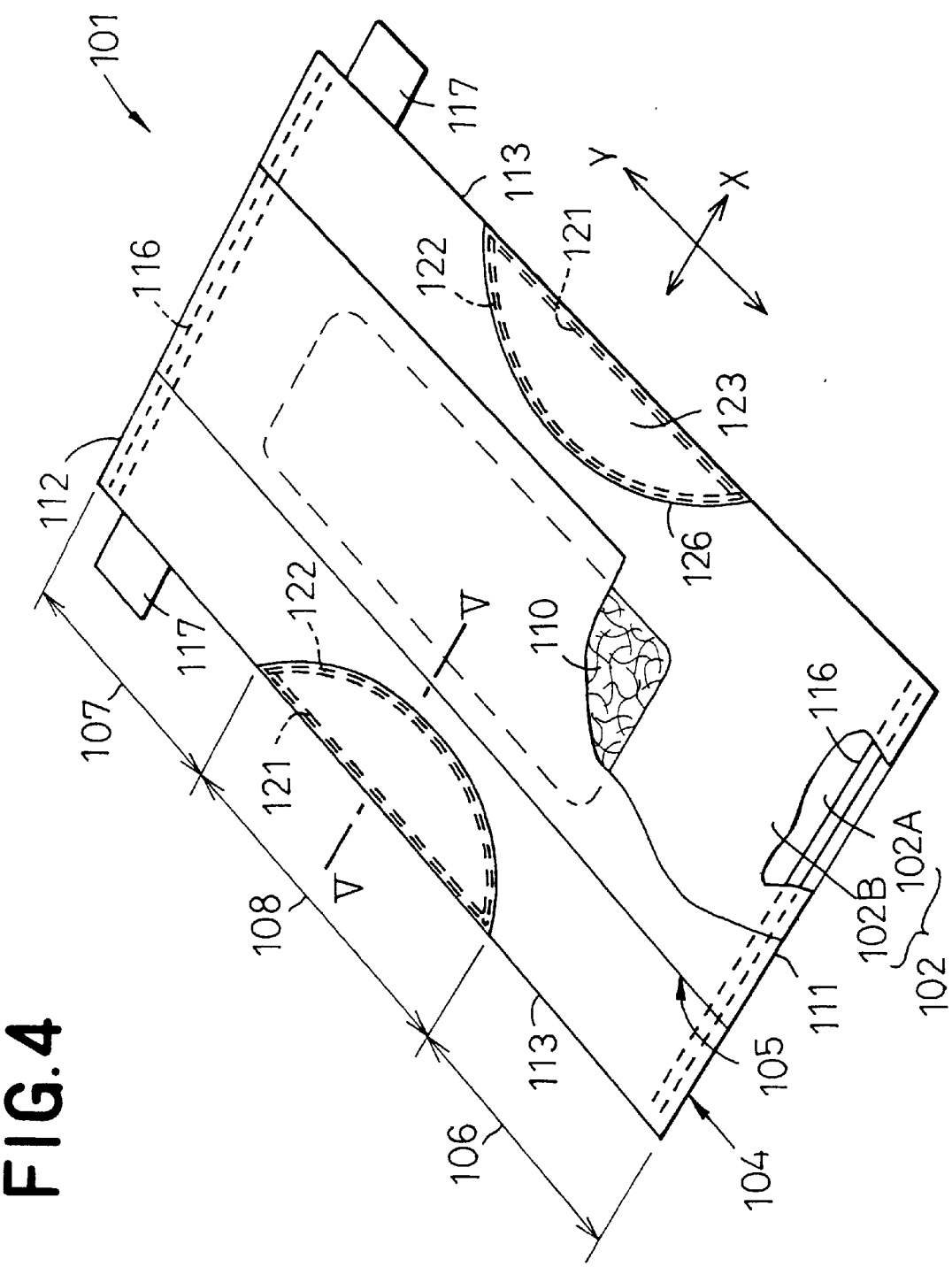
FIG. 4 is a perspective view showing a partially cutaway disposable diaper according to this invention.
Figure 5:
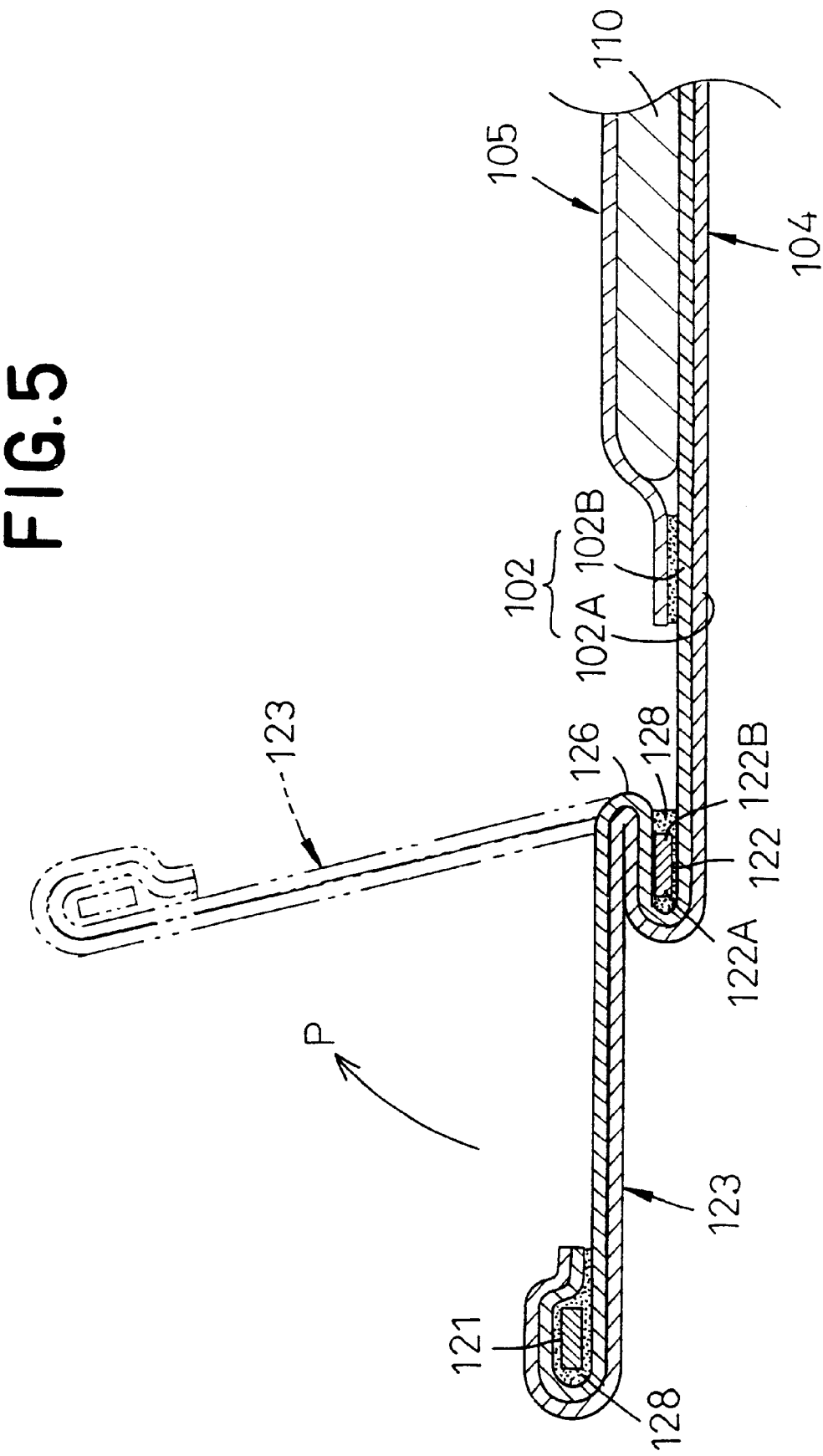
FIG. 5 is a sectional view taken along line V—V in FIG. 4.

FIG. 4 is a perspective view showing another embodiment of this invention in the form of a disposable diaper 101 as partially broken away and FIG. 5 is a sectional view taken along line V—V in FIG. 4. The diaper 101 comprises a backsheet 104 formed by a chassis 102 composed of liquid-impervious plastic film 102A and nonwoven fabric 102B laminated onto the plastic film 102 to define the outer side of the diaper 101, a liquid-pervious topsheet 105 which is identical to the backsheet 104 in its length but narrower than the backsheet 104, and a liquid-absorbent core 110 disposed between these two sheets 104, 105. Portions of the top- and backsheets 104, 105 extending outward beyond a peripheral edge of the core 110 are placed upon and bonded to each other by a hot melt adhesive (not shown). The diaper 101 is of a substantially rectangular shape and contoured by longitudinally front and rear ends 111, 112 extending the direction X and transversely opposite side edges 113 extending parallel to each other between the front and rear ends 111, 112. The diaper 101 is configured to define a front waist region 106, a rear waist region 107 and a crotch region 108 extending between these two waist regions 106, 107 as viewed in the direction Y. Immediately inside the front and rear ends 111, 112, waist-hole elastic members 116 extending in the direction X between the plastic film 102A and the nonwoven fabric 102B and secured under tension to the inner surface of at least one of these plastic film 102A and nonwoven fabric 102B. The rear waist region 107 is provided with a pair of tape fasteners 117 laterally extending from the respective side edges 113. The crotch region 108 is provided with a first leg-hole elastic member 121 extending in the direction Y immediately inside each of one point on the side edges 113 and a second leg-hole elastic member 122 extending from the side edge 113, curving inwardly of the diaper 101, and extending back to another point on said side edge 113. These first and second leg-hole elastic members 121, 122 have their longitudinally opposite ends substantially placed upon or lying closely adjacent one another to form a substantially semicircular side edge zone 123 destined to extend around a wearer's thigh. The core 110 extends between the pair of the second leg-hole elastic members 122.

Referring to FIG. 5, the laminated sheet 102 forming the backsheet 104 is folded inwardly of the diaper 101 along an outer side edge 122A of the second leg-hole elastic member 122, wrapping said elastic member 122, and opposed surfaces of the nonwoven fabric 102B are bonded to each other by an adhesive 128 with the second leg-hole elastic member 122 therebetween. A portion of the laminated sheet 102 now lying inside the elastic member 122 is folded outwardly of the diaper 101 along a fold line 126 extending along the other side edge 122B of the elastic member 122 and thereby the semicircular side edge zone 123 is formed. As will be apparent from FIG. 5, the first leg-hole elastic member 121 is wrapped by the folded side edge of the chassis 102 and secured under tension to the inner side of this folded side edge by an adhesive 128. The second leg-hole elastic member 122 is secured under tension to opposite inner surfaces of the chassis 102 folded in the vicinity of the fold line 126. Contraction of the second leg-hole elastic member 122 causes the side edge zone 123 to rise up in a direction indicated by an arrow P and thereby to form a barrier.

Figure 6:
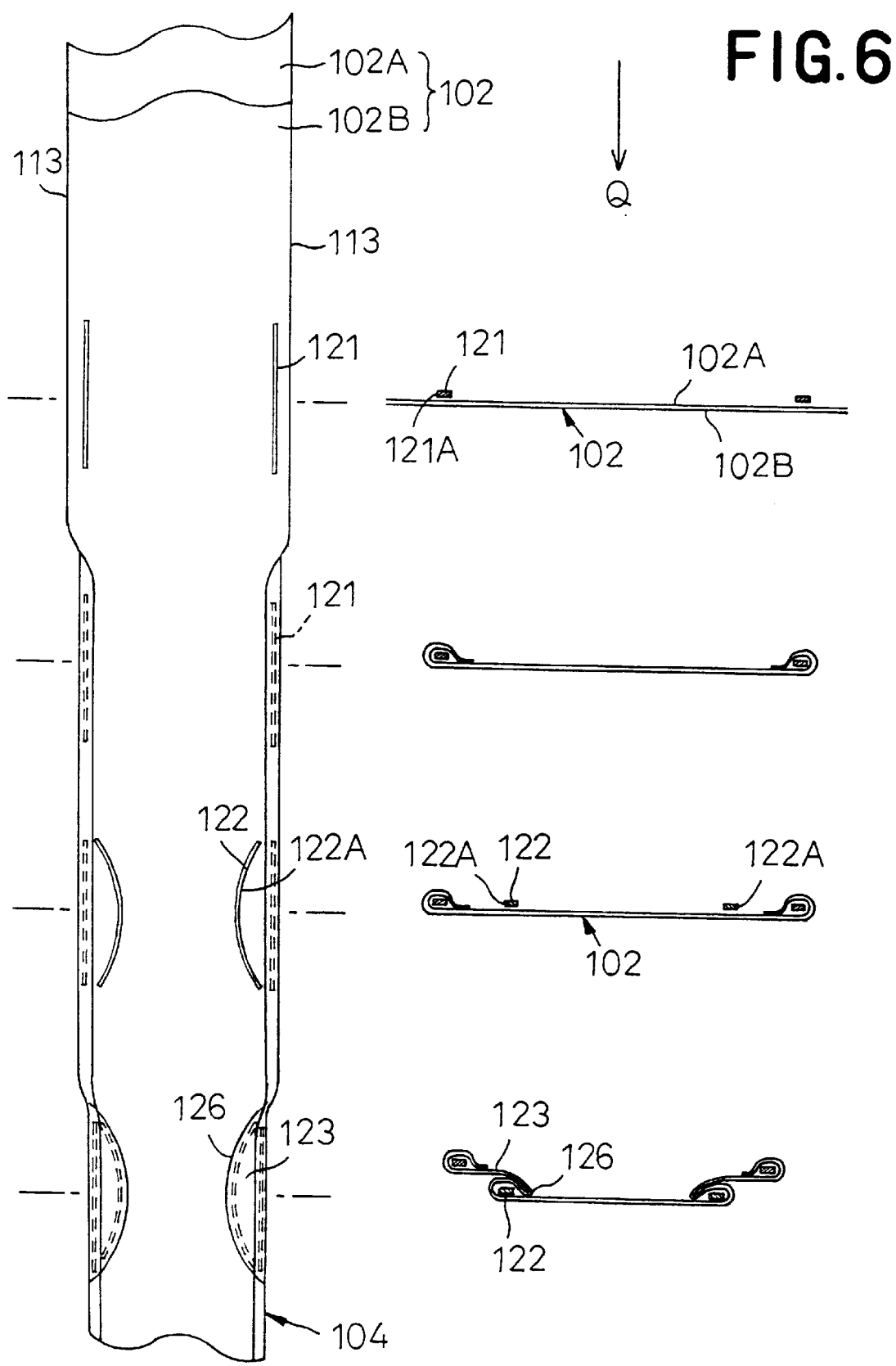
FIG. 6 is a diagram schematically illustrating a process for making a backsheet of the diaper.

FIG. 6 is a diagram exemplarily illustrating a process for continuously making the backsheet 104 of the diaper 101, in which the chassis 102 is illustrated in a sectional view by the side of each step. According to this process, a continuous chassis 102 travels in a longitudinal direction Q and the first leg-hole elastic members 121 are fed under tension onto the chassis 102 so as to be placed upon and bonded to the nonwoven fabric 102B by a hot melt adhesive (not shown) along zones defined immediately inside the transversely opposite side edges 113 of the chassis 102. Then, the chassis 102 is folded back along the outer side edges 121A of the respective members 121 with the nonwoven fabric 102B inside to wrap the respective first leg-hole elastic members 121 and respectively opposed surfaces of the nonwoven fabric 102B are bonded together by a hot melt adhesive. Now the second leg-hole elastic members 122 are fed under tension, describing circular arcs, onto the nonwoven fabric 102B and secured thereto by a hot melt adhesive. Practically at the same time or immediately thereafter, the chassis 102 is folded back along the outer side edges 122A of the elastic members 122 with the nonwoven fabric 102B inside and respectively opposed surfaces of the nonwoven fabric 102B are bonded together by a hot melt adhesive. The semicircular side edge zones are define d between the first and second leg-hole elastic members 121, 122.

The continuous backsheet 104 made in this manner may be cut in an appropriate length to obtain individual backsheets 104. The individual backsheet 104 may be also used as the chassis 2 of the diaper cover 1 shown in FIG. 1. The chassis 102 is slightly tensioned in the longitudinal direction Q as well as in the transverse direction orthogonal to the direction Q as the chassis 102 is folded along the second leg-hole elastic members 122 each describing the circular arcs. In view of such phenomenon, the plastic film 102A and the nonwoven fabric 102B constituting the chassis 102 are preferably stretchable in the longitudinal direction Q as well as in the transverse direction, more preferably, elastically stretchable.

To exploit this invention, securing the two members together may be not only by using an appropriate adhesive but also by heat-sealing at least one of these two members. The chassis 2 or 102 used in the illustrated embodiment may be replaced by a three-layered laminated sheet comprising a pair of nonwoven fabric layers and plastic film disposed between these nonwoven fabric layers or plastic film or nonwoven fabric alone.

What is claimed is:

1. A disposable sanitary garment having inner and outer surfaces, comprising:
   a chassis which defines said outer surface and includes transversely opposed side edge portions which circumferentially extend around a wearer's thighs;
   a pair of first leg-hole elastic members which extend along edges of said side edge portions circumferentially around the wearer's thighs; and
   a pair of second leg-hole elastic members which extend from said edges of said side edge portions along circular arcs that are convex inwardly of a crotch region,
   said chassis being folded back inwardly of said garment along said second leg-hole elastic members so as to wrap around at least two opposite sides of said second leg-hole elastic members and form a folded zone,
   a portion of said chassis which extends inside the folded zone being folded back again outwardly of said garment.

2. The garment according to claim 1, wherein portions of said chassis are folded around and extend on opposite sides of said first and second leg-hole elastic members and are bonded to each of said first and second leg-hole elastic members.

3. The garment according to claim 1, wherein a liquid-absorbent core lies on the inner surface of said chassis between said pair of second leg-hole elastic members.

4. A disposable sanitary garment having inner and outer surfaces, comprising:
   a chassis which defines said outer surface and includes transversely opposed side edge portions which circumferentially extend around a wearer's thighs;
   a pair of first leg-hole elastic members which extend along edges of said side edge portions circumferentially around the wearer's thighs;
   a pair of second leg-hole elastic members which extend from said edges of said side edge portions along circular arcs that are convex inwardly of a crotch region; and
   a liquid absorbent core,
   said chassis being folded back inwardly of said garment along said second leg-hole elastic members so as to wrap said second leg-hole elastic members and form a folded zone,
   a portion of said chassis which extends inside the folded zone being folded back again outwardly of said garment,
   each of said pair of said first leg-hole elastic members and said pair of second leg-hole elastic members being spaced apart transversely outwardly from side edges of the liquid absorbent core.

5. A disposable sanitary garment having inner and outer surfaces, comprising:
   a chassis which defines said outer surface and includes transversely opposed side edge portions which circumferentially extend around a wearer's thighs;
   a pair of first leg-hole elastic members which extend along edges of said side edge portions circumferentially around the wearer's thighs;
   a pair of second leg-hole elastic members which extend from said edges of said side edge portions along circular arcs that are convex inwardly of a crotch region; and
   a liquid absorbent core,
   said chassis being folded back inwardly of said garment along said second leg-hole elastic members so as to wrap said second leg-hole elastic members and form a folded zone,
   a portion of said chassis which extends inside the folded zone being folded back again outwardly of said garment, said portion of the chassis that is folded back again is spaced transversely outwardly from side edges of the liquid absorbent core.

* * * * *